United States Patent [19]

Courty et al.

[11] Patent Number: 4,535,067
[45] Date of Patent: Aug. 13, 1985

[54] CATALYST CONTAINING IRON, CHROMIUM, POTASSIUM AND LANTHANUM OXIDES, ITS MANUFACTURE AND USE IN DEHYDROGENATION REACTIONS

[75] Inventors: Philippe Courty, Houilles; Michel Roussel, Antony; Philippe Varin, Massy; Jean-Francois Le Page, Rueil Malmaison; Serge Leporq, Mantes la Ville, all of France

[73] Assignee: Institut Francais du Petrole, Rueil-Malmaison, France

[21] Appl. No.: 561,376

[22] Filed: Dec. 14, 1983

[30] Foreign Application Priority Data

Dec. 14, 1982 [FR] France ............................. 82 21085
Dec. 14, 1982 [FR] France ............................. 82 21086

[51] Int. Cl.$^3$ ..................... B01J 21/16; B01J 23/10
[52] U.S. Cl. ................................... 502/84; 502/303
[58] Field of Search .................. 502/63, 84, 525, 303

[56] References Cited

U.S. PATENT DOCUMENTS

| | | | |
|---|---|---|---|
| 3,595,809 | 7/1971 | Kehl | 502/525 X |
| 3,897,367 | 7/1975 | Lauder | 502/302 X |
| 4,134,858 | 1/1979 | Courty | 502/63 |
| 4,152,300 | 5/1979 | Riesser | 502/302 |

*Primary Examiner*—Carl F. Dees
*Attorney, Agent, or Firm*—Millen & White

[57] ABSTRACT

There are described catalysts containing, as oxides, iron, chromium and potassium, the latter being optionally partly in form of kaliophyllite $Al_2O_3$, $2 SiO_2$, $K_2O$, as well as lanthanum, in a proportion, calculated in oxide weight, of 1–15% with respect to the final catalyst.

The presence in the catalyst of lanthanum oxide, optionally previously combined with cobalt or vanadium, at least in part in the form of a mixed oxide of the perovskite type, confers to the catalyst an improved activity and/or selectivity in dehydrogenation reactions, particularly of ethylbenzene to styrene.

13 Claims, No Drawings

CATALYST CONTAINING IRON, CHROMIUM, POTASSIUM AND LANTHANUM OXIDES, ITS MANUFACTURE AND USE IN DEHYDROGENATION REACTIONS

BACKGROUND OF THE INVENTION

The present invention relates to new catalysts for use in dehydrogenation reactions and, particularly, in the dehydrogenation of saturated or monoethylenic aliphatic hydrocarbons of low molecular weight (containing, for example, from 2 to 8 carbon atoms) as well as in the dehydrogenation of alkylaromatic hydrocarbons (such as ethylbenzene or diethylbenzenes) to vinylaromatic hydrocarbons (such as styrene or divinylbenzene). It also relates to the manufacture of catalysts and to their use in dehydrogenation processes.

It is known that, in the dehydrogenation of the above-mentioned hydrocarbons, the hydrocarbon is passed, preferably with an additional high proportion of steam (1 to 30 moles $H_2O$/mole hydrocarbon), over a catalyst at an hourly rate by volume, expressed in relation with the liquid hydrocarbon, from 0.05 to 5, preferably from 0.1 to 1 volume (STP) per volume of catalyst and per hour and at a temperature of about 450° to 750° C.

Prior art catalysts have been described for dehydrogenating olefinic hydrocarbons, such as butenes (to butadiene) or alkylaromatic hydrocarbons, such as ethylenebenzene (to styrene), these catalysts containing a major proportion of weight of iron oxide, a potassium compound (oxide or carbonate), vanadium oxide, optionally chromium oxide, as well as a small proportion (from 0.01 to 10% by weight) of at least one additional oxide of a metal such as aluminium, cadmium, copper, magnesium, manganese, nickel, rare earth metals, uranium and zinc. Such catalysts are disclosed in particular in the French Pat. No. 2 387 200 which substantially corresponds to the U.S. Pat. Nos. 4,143,083 and 4,152,300. In these patents, the rare earth metals are defined as metals of atomic number from 58 to 71 included, i.e. from cerium to lutetium. The rare earth metals in the examples are cerium, praseodymium and neodymium.

It has now been discovered as advantageous to use as a rare earth metal, in this type of catalyst, lanthanum (of atomic number 57), which improves the catalytic properties in dehydrogenation reactions (particularly of ethylbenzene to styrene) at low cost.

The French Pat. No. 2 270 003, which corresponds substantially to the U.S. Pat. No. 4,134,858, discloses the use of a clayish material in the manufacture of a dehydrogenation catalyst, mainly based on iron, chromium and potassium oxides. During the thermal activation, at a convenient temperature, generally between 850° and 1100° C., the clayish material combines with potassium oxide to form a double aluminium and potassium silicate (more particularly kaliophyllite). This technique enables one to decrease the filling density of the catalyst.

SUMMARY OF THE INVENTION

The main object of the present invention is to disclose improved catalysts of enhanced activity and/or selectivity as compared to the catalysts of the prior art. Their life time is substantially the same and often longer than that of the known catalysts.

Another object of the invention is to disclose a process for manufacturing said catalysts.

Still another object of the invention is to disclose the use of these catalysts in reaction of hydrocarbons dehydrogenation.

These objects are attained by the catalysts according to the invention, defined generally as containing iron, chromium and potassium oxides in the following ratios by weight:

from 1/1 to 10/1, preferably from 2/1 to 7/1;

from 0.05/1 to 0.4/1, preferably from 0.1/1 to 0.3/1; and

from 15/1 to 40/1, preferably from 25/1 to 35/1;
optionally a double aluminium and potassium silicate, whose composition is more particularly $Al_2O_3$, $2SiO_2$, $K_2O$ (kaliophyllite), in a proportion from 5 to 40% by weight; and a proportion of lanthanum oxide from 1 to 15% by weight, preferably from 3 to 10% by weight.

When the catayst contains a double aluminium and potassium silicate, it contains an excess of potassium oxide with respect to the amount combined as double silicate.

The potassium excess, calculated as oxide, is then in a proportion to iron oxide and chromium oxide corresponding to the following ratios by weight:

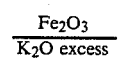

from 3/1 to 10/1; and

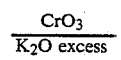

from 0.1 to 0.4/1.

The catalysts according to the invention may further contain a small proportion, for example from 0.1 to 5% by weight, of an oxide of alkali metal other than potassium or of alkaline earth metal (e.g. $Na_2O$, $BaO$, $CaO$).

The catalyst may also contain, in a proportion, as oxide, from 0.1 to 5% of its weight, at least one metal such as cobalt or vanadium.

It is further advantageous that lanthanum be present in the catalyst at least partly combined as mixed oxide with at least one metal such as cobalt or vanadium. The mixed oxide is more particularly of the perovskite type.

For manufacturing the catalysts of the invention, a mixture is formed with water, at least one iron compound, at least one chromium compound, at least one potassium compound and at least one lanthanum compound, in proportions corresponding, as oxides, to the following ratios by weight:

from 1/1 to 10/1, preferably from 2/1 to 7/1,

from 0.05/1 to 0.4/1, preferably from 0.1/1 to 0.3/1,

from 15/1 to 40/1, preferably from 25/1 to 35/1,
the lanthanum compound, calculated as oxide, represents from 1 to 15%, preferably from 3 to 10% by weight of the total reactants, calculated as oxides.

When a clayish material is used, its proportion by weight is about 3.5 to 30% with respect to all the ingredients, calculated as oxides; the potassium compound being used in excess with respect to the amount liable to combine with said clayish material, the potassium excess, in proportion to iron and chromium, calculated as oxides, being in the following ratios by weight:

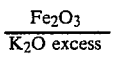

from 3/1 to 10/1; and

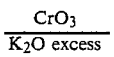

from 0.1/1 to 0.4/1.

The preceeding mixture is then malaxed so as to obtain a paste. The malaxing may be effected by means of a Hobbart mixer or a Warring-Blender.

The obtained paste may then be shaped, for example by extrusion, for example in an Andouart, Hutte, Alexander Werke, O'Toole, or Werner Pfleiderer extruder. The extrudates may consist for example of cylinders of diameter and height between 1 and 7 mm. The drying is generally effected in a stove and the thermal activation may be conducted for example in an electric furnace or in a fuel gas furnace. The drying may be effected for example at 100°–300° C. for 1 to 24 hours, and the calcination from 850° to 1100° C., preferably from 870° to 1050° C., for 1 to 3 hours.

The iron compound is usually ferric iron oxide, finely crushed (e.g. to particles of a size smaller than 200 mesh). The iron oxide is advantageously precalcined at 800° C. For example the product sold by "Société Francaise d'électrometallurgie" (SOFREM) under reference "HA 160" can be used. However, it is possible to replace a portion, for example from 5 to 20% by weight of the total iron oxide, by iron hydroxide, itself obtained by precipitation with ammonia, sodium or potassium of an aqueous solution of iron salts. It is also possible to replace a portion, for example from 5 to 20% by weight, of the total iron oxide by a thermally decomposable iron salt such as iron sulfate, carbonate, acetate, oxalate, citrate, nitrate or alum. Ferrous or ferric iron salts can then be used.

The chromium compounds, used alone or as mixtures, are generally chromic anhydride, chromic salts, e.g. sodium, potassium or ammonium chromate or bichromate, the chromium$^{+3}$ compounds, e.g. nitrate, sulfate, oxide or hydroxide.

The compounds used for introducing potassium, the optional other alkaline metal(s) or alkaline-earth metal(s) (Na, Ca, Ba) as well as cobalt and vanadium are generally the carbonates, oxides and hydroxides. Other salts may also be used, for example sulfates, phosphates or nitrates. As far as vanadium is concerned, vanadates or metavanadates can also be used.

Lanthanum may be introduced as the oxide or as again hydroxide, or as a compound liable to be converted to oxide by heating at a temperature at most equal to that selected for heating the catalyst during its manufacture. Examples of such compounds are carbonates, nitrates, nitrites, sulfides and the organic acid salts, for example the formates, acetates, oxalates, tartrates, citrates, acetylacetonates, and benzoates of said elements.

Examples of clayish materials optionally used to manufacture the catalysts of the invention are given in the French Pat. No. 2 270 003 mentioned above. Preferably kaolinite will be used, for example as Cornouailles kaolin.

Finally a minor proportion of an extrusion aid can be used. Such materials are known in the art and and comprise for example: graphite, vegetal gums (arabic gum, Damhar gum, Carob gum) or alkylcelluloses (methyl-, ethyl- or carboxymethylcelluloses).

All the individual ingredients of the catalyst may be admixed with water to form a paste which is then dried or calcined, or certain ingredients may be introduced after a preliminary treatment destined to form chemical combinations therebetween.

Thus, lanthanum may be introduced as a product resulting from the preliminary reaction of at least one lanthanum compound with at least one compound of at least one metal (M), particularly cobalt or vanadium.

In that preliminary step, the lanthanum compound and the one or more metal M compound(s) are generally used in proportions corresponding to an atomic ratio La/M of from 0.5/1 to 2/1 and more particularly of about 1/1.

In the case of cobalt, the reaction can be effected in solution, between soluble salts, leading to a precipitate, this reaction being followed with the separation of the resultant product (for example by filtration and washing of the precipitate), drying and heating, for example at a temperature from 400° to 950° C. There is thus formed at least a mixed oxide LaCoO$_3$ of the perovskite type.

It can also be conducted by reacting together oxides, or species that thermally decompose to oxides, of lanthanum, on the one hand, and of cobalt or vanadium, on the other hand. In the case of vanadium, introduced in form of a compound of vanadium 5$^+$, it is conducted under a reduced atmosphere (hydrogen), and at a high temperature, for example of from 600° to 900° C. In every case, the catalyst is thereafter subjected to calcination at a temperature of from 900° to 1250° C. The resulting product consists at least partly of a mixed oxide of the perovskite type.

The product obtained in this preliminary step is then admixed with other ingredients and with water and the catalyst manufacture is then continued as above-indicated, by drying and heating at high temperature (for example from 850° to 1100° C.).

The catalysts of the invention, as above-defined, are used for hydrocarbons dehydrogenation, particularly dehydrogenation of aliphatic saturated or monoethylenic hydrocarbons, and alkylaromatic hydrocarbons (ethylbenzene, diethylbenzenes), under known-per-se operating conditions, as above-mentioned.

When used in particular for dehydrogenating ethylbenzene to styrene, the catalysts of the invention provide for a better conversion of ethylbenzene and/or a better selectivity to styrene.

The following examples illustrate the invention, but must not be considered in any way as limiting the scope thereof. Examples 3 to 8, 11, 12 and 15 are given by way of comparison.

EXAMPLE 1 (catalyst A)

300 g of ferric iron oxide "HA 160", 14.5 g of potassium bichromate, 100 g of anhydrous potassium carbonate and 27 g of lanthanum oxide $La_2O_3$ are malaxed in a Warring-Blender.

The reactants amounts correspond, as oxides, to the following proportions (% by weight):
$Fe_2O_3 = 73.23\%$
$CrO_3 = 2.41\%$
$K_2O = 17.77\%$
$La_2O_3 = 6.59\%$ The ratios by weight between iron, chromium and potassium, calculated as oxides, are as follows:

$$\frac{Fe_2O_3}{K_2O} = 4.12; \frac{CrO_3}{K_2O} = 0.135; \frac{Fe_2O_3}{CrO_3} = 30.4$$

67 ml of a 2% by weight aqueous solution of Methocel (sold by DOW CHEMICALS) and 70 ml of water, are then added so as to obtain a firm paste, which is malaxed for 20 minutes and then conveyed to a piston extruder and extruded to elements of 4 mm diameter and 2 to 6 mm length.

The extrudates are dried at 250° C. for 15 hours, then activated for 2 hours at 960° C. Catalyst A is thus obtained.

The analysis of the final catalyst confirms its content of iron, chromium, potassium and lanthanum oxides.

In all the following examples, the malaxing of the ingredients, the extrusion and the drying of the catalysts are effected in the same conditions as in example 1. The activation of the catalysts is effected by heating for 2 hours at temperatures ranging from 940° to 970° C.

EXAMPLE 2 (catalyst B)

300 g of ferric iron oxide "HA 160", 14.5 g of potassium bichromate, 100 g of anhydrous potassium carbonate, 28.5 g of Cornouailles kaolin and 27 g of lanthanum oxide $La_2O_3$ are malaxed in a Warring-Blender. The reactants amounts correspond, as oxides, to the following proportions by weight:
$Fe_2O_3 32 68.47\%$
$CrO_3 = 2.25\%$
$K_2O = 16.62\%$
$La_2O_3 = 6.16\%$
Kaolin = 6.50%

The ratios by weight between iron, chromium and potassium, calculated as oxides, are close to those indicated in example 1.

The potassium amount liable to combine with kaolin corresponds to a proportion by weight, as oxide, of 2.76% with respect to all the oxides. The proportion of potassium oxide "excess" is hence 13.86%.

The ratios between iron oxide and chromium oxide, on the one hand, and $K_2O$ excess, on the other hand, are respectively as follows: (ratios by weight):

$$\frac{Fe_2O_3}{K_2O \text{ excess}} = 4.94; \frac{CrO_3}{K_2O \text{ excess}} = 0.162$$

67 ml of a 2% by weight aqueous solution of Methocel (sold by DOW CHEMICALS) and 70 ml of water are then added so as to form a firm paste. The process is then conducted as indicated in example 1.

The analysis of the final catalyst confirms its content of iron, chromium, potassium and lanthanum oxides. The X-ray diffraction analysis shows the presence of double aluminium and potassium silicate (kaliophyllite) in a proportion by weight of 9.3%.

EXAMPLES 3 TO 5 (catalysts C to E)

The preparation of example 1 is repeated, except that, instead of lanthanum oxide $La_2O_3$, an equal amount by weight of another rare earth oxide is used:
Example 3: cerium oxide $CeO_2$ (catalyst C)
Example 4: praseodymium oxide $Pr_8O_{11}$ (catalyst D)
Example 5: neodymium oxide $NdO_3$ (catalyst E)

EXAMPLES 6 TO 8 (catalysts F to H)

The preparation of example 2 (catalyst B) is repeated, except that, instead of lanthanum oxide $La_2O_3$, an equal amount by weight of another rare earth oxide is used:
Example 6: cerium oxide $CeO_2$ (catalyst F)
Example 7: praseodymium oxide $Pr_8O_{11}$ (catalyst G)
Example 8: neodymium oxide $NdO_3$ (catayst H)

EXAMPLE 9 (catalyst I)

300 g of ferric iron oxide "HA 160", 14.5 g of potassium bichromate, 100 g of anhydrous potassium carbonate, 28.5 g of Cornouailles kaolin, 17.9 g of lanthanum oxide, 9.1 g of cobalt oxide $Co_2O_3$ are malaxed in a Warring-Blender. The same atomic amounts of lanthanum and cobalt have been selected.

The reactants amounts, expressed as oxides, correspond to the following proportions (% by weight):
$Fe_2O_3 = 68.47\%$
$CrO_3 = 2.25\%$
$K_2O = 16.62\%$
$La_2O_3 = 4.08\%$
$Co_2O_3 = 2.08\%$
Kaolin = 6.50%

50 ml of a 2% by weight Methocel aqueous solution and 100 ml of water are added to form a paste which is malaxed for 15 minutes. The extrusion, drying and calcining of the catalyst are effected as above-indicated.

The content of double aluminium and potassium silicate (koliophyllite) in the final catalysts is close to 9.3% by weight.

EXAMPLE 10 (catalyst J)

The preparation of example 9 (catalyst I) is repeated, except that, instead of cobalt oxide $Co_2O_3$, an equal amount by weight of vanadic anhydride $V_2O_5$ is used.

The reactants amounts correspond, as oxides, to the following proportions (% by weight):
$Fe_2O_3 = 68.47\%$
$CrO_3 = 2.25\%$
$K_2O = 16.62\%$
$La_2O_3 = 4.08\%$
$V_2O_5 = 2.08\%$ Kaolin=6.50%

The ratios by weight between iron, chromium and potassium, calculated as oxides, have values close to those indicated in example 1.

The analysis of the final catalyst confirms the content of iron, chromium, potassium, lanthanum and vanadium oxides.

EXAMPLE 11 (catalyst K)

The preparation of example 9 (catalyst I), is repeated, except that, instead of lanthanum oxide, an equal amount by weight of cerium oxide $CeO_2$ is used.

EXAMPLE 12 (catalyst L)

The preparation of example 10 (catalyst J) is repeated, except that, instead of lanthanum oxide $La_2O_3$, an equal amount by weight of cerium oxide $CeO_2$ is used.

EXAMPLE 13 (catalyst M)

145.5 g of cobalt nitrate and 190 ml of a 2.63 moles/l lanthanum nitrate aqueous solution are poured into 2.5 l of water at 80° C. containing 212 g of $Na_2CO_3$. The reactants amounts correspond to a cobalt to lanthanum atomic ratio of 1/1.

The resultant precipitate is washed with 12 liters of distilled water.

After maturation for 6 hours at 80° C., the product is filtered and dried for 24 hours at 50° C., 72 hours at 100° C., and then 24 hours at 120° C. A final heating is performed for 2 hours, at 600° C.

The structure of the resultant product was not identified with certainty. It seems to be formed, at least partially, of a mixed oxide of the perovskite type $LaCoO_3$.

27 g of the so-prepared product are admixed with 300 g of ferric iron oxide "HA 160", 14.5 g of potassium bichromate, 100 g of anhydrous potassium carbonate and 28.5 g of Cornouailles kaolin.

The reactants amounts correspond, as oxides, to the following proportions (% by weight):

$Fe_2O_3$=68.47%
$CrO_3$=2.25%
$K_2O$=16.62%
$LaCoO_3$=6.16%
Kaolin=6.50%

The process is then conducted under the same conditions as above-indicated.

EXAMPLE 14 (catalyst N)

163 g of lanthanum oxide $La_2O_3$ and 91 g of vanadic anhydride $V_2O_5$ are thouroughly mixed and heated in a tubular furnace under a hydrogen stream at 850° C. for 6 hours and then calcined for 18 hours at 1200° C. The involved amounts of the reactants correspond to an atomic ratio La/V of about 1/1. The product obtained consists at least partially of a mixed oxide $LaVO_3$ of the perovskite type.

It is then operated as described in example 13.

EXAMPLE 15 (Catalyst O)

The preparation of example 14 (catalyst N) is repeated except that the mixed oxide preliminarily formed between lanthanum and vanadium is replaced by an equal amount by weight of mixed oxide preliminarily formed between cerium and vanadium, in atomic proportion Ce/V of about 1/1.

Catalysts A to O have been subjected to a catalyst long run test.

The catalyst test is effected in a "catatest" operating under atmospheric pressure and fed with ethylbenzene of industrial grade and water. The tested catalyst volume is 100 ml (60 to 120 g of catalyst). The catalysts A to O are shaped as extrudates of 4 mm diameter and 4–5 mm length.

The catalyst is first preheated up to about 500° C. Steam is introduced, and then, at about 550° C., ethylbenzene is introduced. The temperatures are then adjusted so as to obtain a temperature of 614±2° C. in the catalyst bed.

The hourly flow rates are as follows:

$$\frac{\text{Ethylbenzene}}{\text{Catalyst}} = 0.4 \text{ volume } v^{-1}h^{-1} \quad \frac{H_2O}{\text{Ethylbenzene}} = 2 \text{ g g}^{-1}$$

Table I indicates the conversion rate of ehtylbenzene ($C_{EB}$), the selectivity to styrene ($S_{ST}$) and the yield to styrene ($Y_{ST}$). These figures are expressed in mole % and correspond to the following definitions:

$$C_{EB} = \frac{\text{moles of converted ethylbenzene}}{\text{moles of supplied ethylbenzene}} \times 100$$

$$S_{ST} = \frac{\text{moles of ethylbenzene converted to styrene}}{\text{moles of converted ethylbenzene}} \times 100$$

$$Y_{ST} = \frac{\text{moles of produced styrene}}{\text{moles of supplied ethylbenzene}} \times 100$$

These values are linked by the relationship:

$$Y_{ST} = C_{EB} \times S_{ST} \times \frac{1}{100}$$

TABLE I

| Catalyst | A | B | C | D | E | F | G | H | I | J | K | L | M | N | O |
|---|---|---|---|---|---|---|---|---|---|---|---|---|---|---|---|
| Example | 1 | 2 | 3 | 4 | 5 | 6 | 7 | 8 | 9 | 10 | 11 | 12 | 13 | 14 | 15 |
| Convers. EB % mol. | 59.9 | 60.0 | 60.1 | 59.4 | 58.8 | 60.2 | 59.5 | 59.0 | 61.0 | 60.0 | 60.5 | 60.1 | 65.9 | 61.0 | 60.5 |
| Select. ST % mol. | 92.0 | 92.1 | 90.1 | 92.5 | 92.4 | 90.0 | 92.5 | 92.5 | 90.5 | 92.3 | 90.1 | 90.5 | 91.9 | 92.0 | 90.4 |
| Yield ST % mol. | 55.1 | 55.3 | 54.1 | 54.9 | 54.3 | 54.2 | 55.0 | 54.6 | 55.2 | 55.4 | 54.5 | 54.4 | 60.5 | 56.1 | 54.7 |

In Table I, the comparison between catalyst A and catalysts C, D and E, the comparison between catalyst B and catalysts F, G and H, the comparison between catalyst I and catalyst K, the comparison between catalyst J and catalyst L and the comparison between catalyst N and catalyst O show that the use of lanthanum results in improvements in the yield to styrene as compared with the use of other rare earths: cerium, praseodymium, neodymium, this being true either with the rare earth metal used as the only additional metal (in addition to iron, chromium and potassium), with or without addition of kaolin, or with the rare earth metal associated to another additional metal in the form of two separate metal compounds or in the form of associated oxides prepared in a preliminary step (case of associations with cobalt and vanadium).

What is claimed as the invention is:

1. A catalyst comprising, as oxides, iron, chromium and potassium, the iron, chromium and potassium, calculated as oxides, being in proportion corresponding to ratios by weight:

$$\frac{FeO_3}{K_2O}$$

from 1/1 to 10/1

$$\frac{CrO_3}{K_2O}$$

from 0.05/1 to 0.4/1

$$\frac{Fe_2O_3}{CrO_3}$$

from 15/1 to 40/1,
characterized in that it also comprises, as oxide, lanthanum in a proportion, calculated as oxide, from 1 to 15% by weight with respect to the catalyst weight.

2. A catalyst according to claim 1, characterized in that it comprises kaliophyllite of the formula $Al_2O_3$, $2SiO_2$, $K_2O$ and an excess of potassium with respect to that comprised in kaliophyllite, the kaliophyllite proportion being from 5 to 40% of the catalyst weight, the potassium excess being, in proportion to iron and chromium, in the following ratios by weight:

$$\frac{Fe_2O_3}{K_2O\text{ excess}} = 3/1 \text{ to } 10/1 \text{ and } \frac{CrO_3}{K_2O\text{ excess}} = 0.1/1 \text{ to } 4/1.$$

3. A catalyst according to one of claims 1 or 2, characterized in that the ratios by weight between iron, chromium and potassium, calculated as oxides, are:

$$\frac{Fe_2O_3}{Total\ K_2O}$$

from 2/1 to 7/1;

$$\frac{CrO_3}{Total\ K_2O}$$

from 0.1/1 to 0.3/1; and $$\frac{Fe_2O_3}{CrO_3}$$

from 25/1 to 35/1,
and the lanthanum proportion, calculated as oxide, is from 3 to 10% by weight.

4. A catalyst according to one of claims 1 or 2, characterized in that it also comprises, calculated as oxide, from 0.1 to 5% by weight of at least one metal selected from cobalt and vanadium.

5. A process for manufacturing a catalyst according to claim 1, characterized in that:
 a. a mixture comprising water, at least one iron compound, at least one chromium compound, at least one potassium compound and at least one lanthanum compound, is malaxed to form a paste and,
 b. said paste is dried, as such or after shaping, and is thermally activated at a temperature from 850° to 1100° C.,
the iron, chromium and potassium compounds being used in proportions corresponding, as oxides, to the following ratios by weight:

$$\frac{Fe_2O_3}{K_2O}$$

from 1/1 to 10/1;

$$\frac{CrO_3}{K_2O}$$

from 0.05/1 to 0.4/1; and $$\frac{Fe_2O_3}{CrO_3}$$

from 15/1 to 40/1,
and the lanthanum compound being used in a proportion, calculated as oxide, from 1 to 15% by weight of the totality of the compounds involved.

6. A process according to claim 5, characterized by the addition of at least one compound of at least one metal selected from cobalt and vanadium to the metal compounds of step (a), the total content of added metals, expressed as oxides, being from 0.1 to 5% by weight of the totality of the compounds involved.

7. A process according to claim 6, characterized in that, in step (a), a clayish material is used in a proportion from 3.5 to 30% by weight, the potassium compound is used in excess with respect to the amount liable to combine with said clayish material, the potassium compound excess being in a proportion to iron and chromium, calculated as oxides, corresponding to the ratios by weight:

$$\frac{Fe_2O_3}{K_2O\text{ excess}} \text{ from } 3/1 \text{ to } 10/1 \quad \frac{CrO_3}{K_2O\text{ excess}} \text{ from } 0.1/1 \text{ to } 0.4/1$$

8. A process according to claim 7, characterized in that said clayish material is comprised at least partly of kaolinite.

9. A process according to one of claims 5 to 8, characterized in that the activation temperature of step (b) is from 870° to 1050° C.

10. A catalyst according to claim 3, characterized in that it also comprises, calculated as oxide, from 0.1 to 5% by weight of at least one metal selected from cobalt and vanadium.

11. A process according to claim 5, characterized in that, in stap (a), a clayish material is used in a proportion from 3.5 to 30% by weight, the potassium compound is used in excess with respect to the amount liable to combine with said clayish material, the potassium compound excess being in a proportion to iron and chromium, calculated as oxides, corresponding to the ratios by weight:

$$\frac{Fe_2O_3}{K_2O\text{ excess}} \text{ from } 3/1 \text{ to } 10/1 \quad \frac{CrO_3}{K_2O\text{ excess}} \text{ from } 0.1/1 \text{ to } 0.4/1.$$

from 0.1/1 to 0.4/1.

12. A process according to claim 11, characterized in that said clayish material consists at least partly of kaolinite.

13. A process according to claim 12, characterized in that the activation temperature of step (b) is from 870° to 1050° C.

* * * * *